(12) United States Patent
Hess et al.

(10) Patent No.: US 7,349,819 B2
(45) Date of Patent: Mar. 25, 2008

(54) METHOD FOR PROVIDING ROBUSTNESS TO THE SOLUTION OF THE CUBIC EQUATION OF STATE

(75) Inventors: Todd M. Hess, Chagrin Falls, OH (US); Yang Su, Katy, TX (US); Prasad V. Shertukde, Hudson, OH (US)

(73) Assignee: ABB Inc., Norwalk, CT (US)

( * ) Notice: Subject to any disclaimer, the term of this patent is extended or adjusted under 35 U.S.C. 154(b) by 981 days.

(21) Appl. No.: 10/615,284

(22) Filed: Jul. 8, 2003

(65) Prior Publication Data
US 2005/0010629 A1    Jan. 13, 2005

(51) Int. Cl.
*G06F 19/00* (2006.01)

(52) U.S. Cl. ............ 702/98; 702/22; 324/353; 73/861.08

(58) Field of Classification Search ........... 702/98, 702/22, 182–185; 324/353; 73/1.37, 1.57, 73/861.08
See application file for complete search history.

(56) References Cited

U.S. PATENT DOCUMENTS

2004/0260497 A1* 12/2004 DiFoggio et al. ............ 702/98

* cited by examiner

*Primary Examiner*—Edward Raymond
(74) *Attorney, Agent, or Firm*—Michael M. Rickin (57) ABSTRACT

The cubic equations of state (CEOS) relate pressure, temperature and molar volume of a mixture. The deviation of the physical properties of a mixture from ideality is expressed by the compressibility factor. The compressibility factor is calculated from the CEOS. There is described a solution to the CEOS which provides a continuous solution for compressibility factors over the entire range of operating conditions. This solution avoids the non-unique roots, trivial roots and singularities that are present in the prior art solutions of the CEOS.

16 Claims, 4 Drawing Sheets

METHOD FOR PROVIDING ROBUSTNESS TO THE SOLUTION OF THE CUBIC EQUATION OF STATE

FIELD OF THE INVENTION

This invention relates to models which are used in process simulation and more particularly to the cubic equations of state.

DESCRIPTION OF THE PRIOR ART

The use of computer simulations to develop new processes, design and retrofit plants, and optimize the operation of existing plants is widely practiced in the process industry. Throughout process design, development, and operation, the mathematical models that are used in process simulation can be used to make better engineering and business decisions. Rigorous models require complex numerical solvers. The stability of the numerical solvers can be improved by using integrated physical property calculation solvers.

The cubic equations of state (CEOS) relate pressure, temperature and molar volume of a mixture. The deviation of the physical properties of a mixture from ideality is expressed by the compressibility factor. The compressibility factor is calculated from the CEOS, where the compressibility factor is a function of volume terms raised to third power. The CEOS offers the advantage of using very few standard physical properties (critical pressure, critical temperature, critical compressibility factor, critical volume, and accentric factor) as input to evaluate the actual compressibility factor.

All other physical property equations are functions of the compressibility factor. These include fugacity, enthalpy, entropy, viscosity, volume, density, and internal energy. The most commonly used forms of CEOS are Soave-Redlich-Kwong (SRK), Peng-Robinson (PR), Redlich-Kwang (RK), and Ideal equations of state.

The solution to the CEOS to compute the compressibility factor encounters three problems:

non-unique roots;

trivial roots; and singularities.

The two phase Vapor-Liquid equilibrium region is discontinuous in nature. The solution of the CEOS in a two phase Vapor-Liquid equilibrium region can sometimes result in three non-unique roots. In a narrow region of physical conditions, the CEOS can give one valid root for the liquid phase and one valid root for the vapor phase. Under most conditions of pressure, temperature, and composition, however, no root can be found either for the vapor phase or the liquid phase. This is known as a trivial roots problem and is commonly encountered over a wide range of operating conditions. The third numerical problem, singularity, arises when the valid root happens to be at a local maximum or minimum of a pressure-volume curve. This represents infinite possible values of derivatives of dependent properties such as K value, enthalpy departure, and fugacity coefficients.

Physical property prediction tools have overcome these deficiencies by identifying vapor, liquid and vapor-liquid regions to determine the conditions necessary to identify solution of the CEOS. However, these procedures can sometimes not be particularly robust, especially when a system either approaches or experiences a discontinuity during the course of the solution.

The prior art property prediction tools are described in:
1. Poling B. E., Prausnitz J. M., O'Connell J. P., The Properties of Gases & Liquids, $5^{th}$ edition, McGraw-Hill, November 2000 ("Poling et al.").
2. Agarwal R, Li Y. K., Santollani O., Satyro M. A., Vieler A., Uncovering the Realities of Simulation Part II, Chemical Engineering Progress, pp 64–72, June 2001 ("Agarwal et al.").
3. Twu C. H., Sim W. D., Tassone V., Getting a Handle on Advanced Cubic Equations of State, Chemical Engineering Progress, pp. 58–65, November 2002 ("Twu et al.).

The present invention defines a procedure whereby the solution of the CEOS can be represented in continuous form overcoming many of the robustness issues experienced by the prior art. In arriving at the solution of the present invention it was determined that the problems in the solution of the CEOS, namely, non-unique roots, trivial roots and singularities were primarily responsible for the failure of the solver. Thus the method of the present invention was developed to eliminate all of these problems and generate a continuous solution for compressibility factors over the entire range of operating conditions.

SUMMARY OF THE INVENTION

A method for calculating the compressibility factors of a mixture using the cubic equation of state (CEOS). The mixture has a liquid region. The method comprises:

a) calculating a pure liquid compressibility factor when the compressibility factor is in the liquid region;

b) using the second virial coefficient of the CEOS to determine from the pure liquid compressibility factor a vapor compressibility factor extensible in the liquid region; and c) accepting the higher of the pure liquid compressibility factor or the vapor compressibility factor extensible in the liquid region.

A method for calculating the compressibility factors of a mixture using the cubic equation of state (CEOS). The mixture has a vapor-liquid equilibrium region. The method comprises:

a) determining that the compressibility factor is in the vapor-liquid equilibrium region;

b) calculating when the compressibility factor is in the vapor-liquid equilibrium region a pure liquid compressibility factor;

c) using the virial coefficients of the CEOS and the pure liquid compressibility factor calculated when the compressibility factor is in the vapor-liquid equilibrium region to determine a vapor compressibility factor in the vapor-liquid equilibrium region; and d) accepting the higher of the pure liquid compressibility factor calculated when the compressibility factor is in the vapor-liquid equilibrium region or the vapor compressibility factor calculated in the vapor-liquid equilibrium region.

A method for calculating the compressibility factors of a mixture using the cubic equation of state (CEOS). The mixture has a vapor-liquid equilibrium region. The method comprises:

a) calculating a pure liquid compressibility factor for the vapor-liquid equilibrium region;

b) using the virial coefficients of the CEOS and the pure liquid compressibility factor calculated for the vapor-liquid equilibrium region to determine a vapor compressibility factor in the vapor-liquid equilibrium region; and c) accepting the higher of the pure liquid compressibility factor calculated for the vapor-liquid equilibrium region or the vapor compressibility factor calculated in the vapor-liquid equilibrium region.

A method for calculating the compressibility factors of a mixture using the cubic equation of state (CEOS). The mixture has a liquid region and a vapor-liquid equilibrium region. The method comprises:

determining that the compressibility factor is either in the liquid region or in the vapor-liquid equilibrium region;

the method when the compressibility factor is in the liquid region comprising:

calculating a pure liquid compressibility factor;

using the second virial coefficient of the CEOS to determine from the pure liquid compressibility factor a vapor compressibility factor extensible in the liquid region; and accepting the higher of the pure liquid compressibility factor or the vapor compressibility factor extensible in the liquid region;

the method when the compressibility factor is in the liquid region comprising:

calculating a pure liquid compressibility factor;

using the virial coefficients of the CEOS and the pure liquid compressibility factor to determine a vapor compressibility factor in the vapor-liquid equilibrium region; and accepting the higher of the pure liquid compressibility factor or the vapor compressibility factor calculated in the vapor-liquid equilibrium region.

A method for calculating the compressibility factors of a mixture using the cubic equation of state (CEOS). The mixture has a liquid region and a vapor-liquid equilibrium region. The method comprises:

a) calculating a pure liquid compressibility factor when the compressibility factor is in the liquid region;

b) using the second virial coefficient of the CEOS to determine from the pure liquid compressibility factor a vapor compressibility factor extensible in the liquid region; and c) accepting the higher of the pure liquid compressibility factor or the vapor compressibility factor extensible in the liquid region;

d) calculating a pure liquid compressibility factor for the vapor-liquid equilibrium region;

e) using the virial coefficients of the CEOS and the pure liquid compressibility factor calculated for the vapor-liquid equilibrium region to determine a vapor compressibility factor in the vapor-liquid equilibrium region; and f) accepting the higher of the pure liquid compressibility factor calculated for the vapor-liquid equilibrium region or the vapor compressibility factor calculated in the vapor-liquid equilibrium region.

A method for calculating the liquid compressibility factor of a mixture using the cubic equation of state (CEOS). The mixture has a liquid region. The method comprises:

a) calculating a pure liquid compressibility factor when the compressibility factor is in the liquid region;

b) determining that the rate of change of the pure liquid compressibility factor with temperature is or is not less than zero; and c) accepting the pure liquid compressibility as the liquid compressibility factor when the pure liquid compressibility factor rate of change is not less than zero.

A computer readable medium having instructions for causing a computer to execute a method for calculating the compressibility factors of a mixture using the cubic equation of state (CEOS), the mixture having a liquid region. The instructions comprise:

a) calculating a pure liquid compressibility factor when the compressibility factor is in the liquid region;

b) using the second virial coefficient of the CEOS to determine from the pure liquid compressibility factor a vapor compressibility factor extensible in the liquid region; and c) accepting the higher of the pure liquid compressibility factor or the vapor compressibility factor extensible in the liquid region.

A computer readable medium having instructions for causing a computer to execute a method for calculating the compressibility factors of a mixture using the cubic equation of state (CEOS), the mixture having a vapor-liquid equilibrium region. The instructions comprise:

a) calculating a pure liquid compressibility factor for the vapor-liquid equilibrium region;

b) using the virial coefficients of the CEOS and the pure liquid compressibility factor calculated for the vapor-liquid equilibrium region to determine a vapor compressibility factor in the vapor-liquid equilibrium region; and c) accepting the higher of the pure liquid compressibility factor calculated for the vapor-liquid equilibrium region or the vapor compressibility factor calculated in the vapor-liquid equilibrium region.

A computer readable medium having instructions for causing a computer to execute a method for calculating the compressibility factors of a mixture using the cubic equation of state (CEOS), the mixture having a liquid region. The instructions comprise:

a) calculating a pure liquid compressibility factor when the compressibility factor is in the liquid region;

b) determining that the rate of change of the pure liquid compressibility factor with temperature is or is not less than zero; and c) accepting the pure liquid compressibility as the liquid compressibility factor when the pure liquid compressibility factor rate of change is not less than zero.

DESCRIPTION OF THE PREFERRED EMBODIMENT(S)

Figure 1:
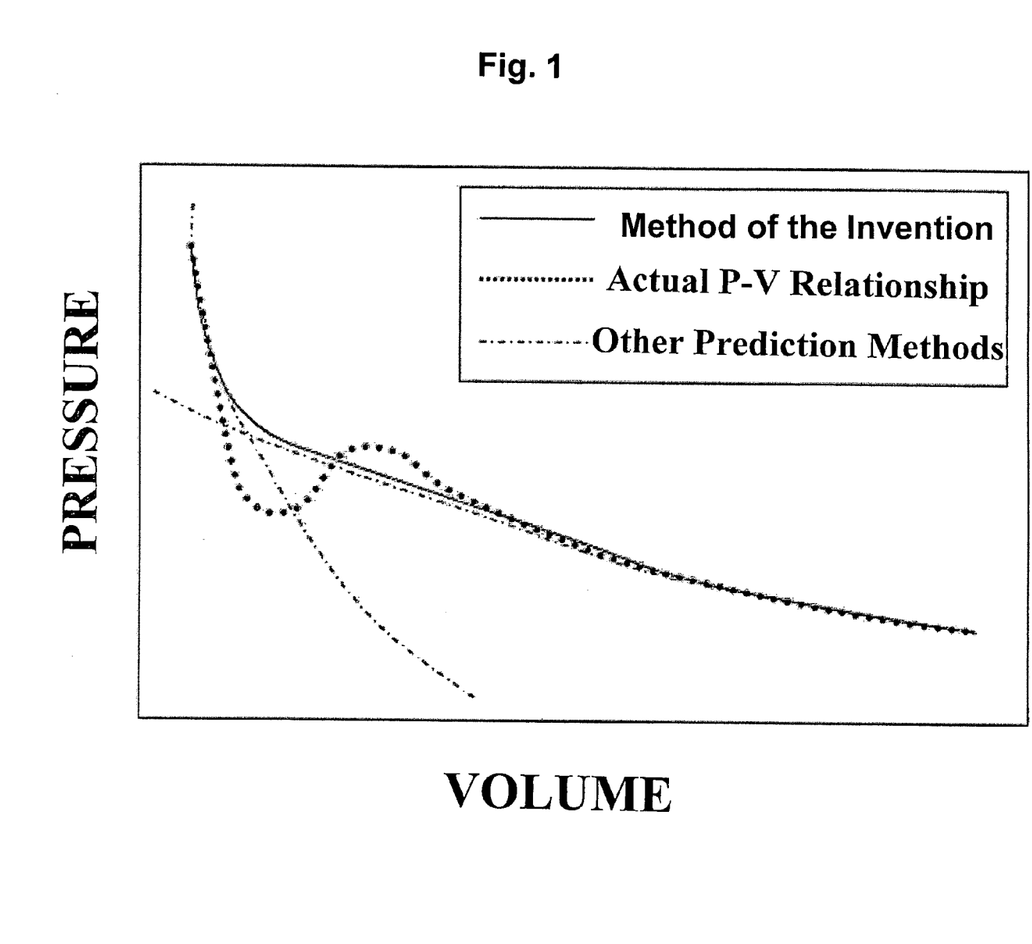
FIG. 1 shows a typical pressure(P)-volume(V) relationship for a hydrocarbon compound.

Referring now to FIG. 1 there is shown by a dotted line a typical pressure (P)-volume(V) relationship for a hydrocarbon compound. The P-V relationship has, as is described in Poling et al., three distinct regions. A high pressure region 10 representing the liquid phase, shows a sharp variation. A low pressure 12 region representing the vapor phase shows a slow variation. An intermediate region 14 representing vapor-liquid equilibrium region shows a moderate variation with a complex behavior. The P-V relationship in the vapor-liquid equilibrium region is not smooth and can have local maxima 14$a$ and minima 14$b$ as is shown in FIG. 1.

While the techniques of the prior art described in Poling et al., Agarwal et al. and Twu et al. can as is shown by the dashed lines in FIG. 1 closely approximate the pure vapor and pure liquid regions they deviate from the actual data in the vapor-liquid equilibrium region. The prior art has tried several approaches to overcome this deviation, including extension of pure vapor in to liquid phase and extension of pure liquid in to vapor phase. These approaches fail to approximate the vapor-liquid region as the prior art solutions are almost always unstable and inaccurate in that region.

The methods of the present invention implemented for solving the CEOS for the vapor and liquid compressibility factors can as is shown in FIG. 1 by the solid line closely approximate the pure liquid and vapor region as well as the vapor-liquid equilibrium region. These methods are described below. The method of the present invention is focused on the P-V prediction in the vapor-liquid equilibrium region by:

(a) improving stability
(b) improving accuracy

Figure 2:
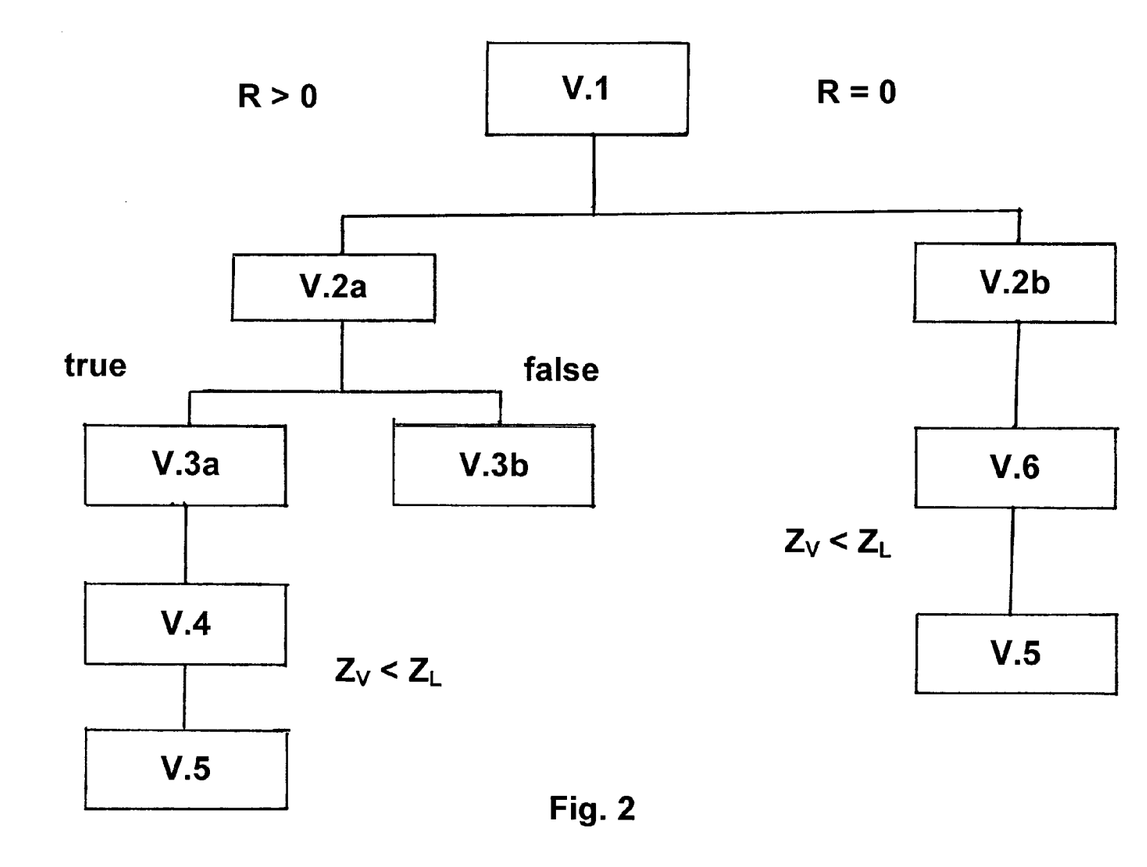
FIG. 2 is the flowchart for the method of the present invention to calculate the vapor compressibility factor.
Figure 3:
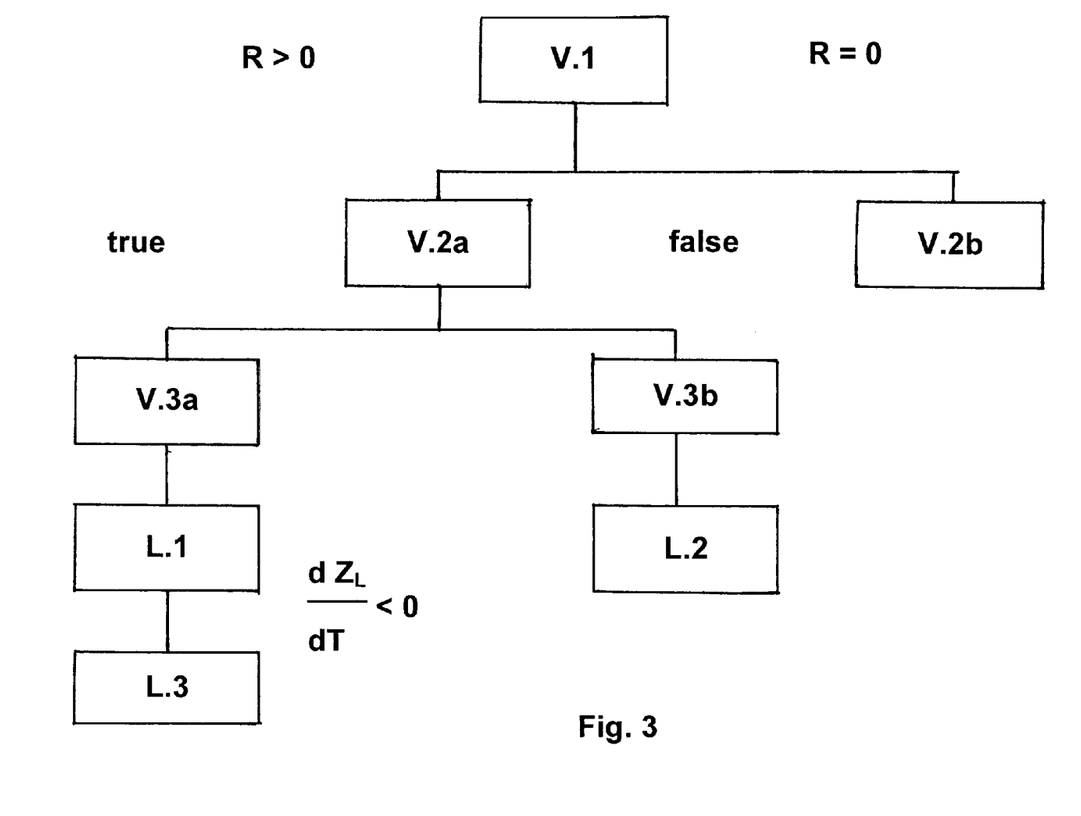
FIG. 3 is the flowchart for the method to calculate the liquid compressibility factor.

FIG. 2 is the flowchart for the method to calculate the vapor compressibility factor and FIG. 3 is the flowchart for the method to calculate the liquid compressibility factor.

As is described in Poling et al. and Agarwal et al., the CEOS that is solved to obtain the value of Z, the compressibility factor, is $$Z^3 + B*Z^2 + C*Z + D = 0 \quad (E.1)$$

where the parameters B, C, and D are known as second, third and fourth virial coefficients. For example, under the Soave-Redlich-Kwong system, their definitions are as follows:

$$B = -1$$

$$C = A^* - B^* - B^{*2}$$

$$D = -A^* * B^*$$

Where $$A^* = \frac{aP}{R^2 T^2}$$

$$B^* = \frac{bP}{RT}$$

Calculations for $Z_V$, Vapor Compressibility Factor

Once the B, C, and D values are computed, the solver goes through the sequence of equations and conditions shown in FIG. 2 and described below to determine the compressibility factor. The sequence of equations and conditions followed by the solver depends on the value of R. The method follows the CEOS solution in the vapor region. It uses liquid compressibility as an extension of vapor compressibility in the liquid region. The equations described below are used to smooth out the $Z_V$ calculations during transition from vapor to vapor-liquid to liquid region.

Equations Used in Calculation Of $Z_V$ $$R = \frac{\left(\frac{3*C - B^2}{3}\right)^3}{27} + \frac{\left(\frac{27*D - 9*B*C + 2*B^3}{27}\right)^2}{4} \quad (V.1)$$

where the value of the variable R determines the possible solutions of the CEOS.

When R>0, the CEOS has only one real root and two conjugate complex roots. The solution is either in a pure vapor or pure liquid region. In the vapor region, the compressibility factor for pure vapor is accepted. In the liquid region, the compressibility factor for pure liquid is accepted as an extension of the vapor compressibility factor. It should be noted that it is a common practice to hypothetically extend the pure vapor solution in to the pure liquid region. However, this can cause a sharp change in compressibility factor leading to instability in the solver.

When R≦0, the CEOS can have either two or three roots. When R=0 there are three real roots and at least two of them are equal. When R<0 the solution is three unequal roots. The solution falls in the vapor-liquid equilibrium region. This is where state changes occur and the solution of the CEOS becomes discontinuous The solution faces, as was described above, problems of non-unique roots, trivial roots and singularities.

This overall scheme is elaborated in following discussion.

$$\sqrt{R} > -\left(\frac{27*D - 9*B*C + 2*B^3}{54}\right) \quad (V.2a)$$

$$Z_L = -2*\sqrt{\frac{B^2 - 3*C}{9}} \quad (V.2b)$$

$$\left\{\cos\left(\frac{a\cos\left[\frac{27*D - 9*B*C + 2*B^3}{2*\sqrt{-(3*C - B^2)^3}}\right]}{3}\right)\right\} - \frac{B}{3}$$

$$Z_L = \sqrt[3]{-\left(\frac{27*D - 9*B*C + 2*B^3}{54}\right) + \sqrt{R}} + \quad (V.3a)$$

$$\sqrt[3]{-\left(\frac{27*D - 9*B*C + 2*B^3}{54}\right) - \sqrt{R}} - \frac{B}{3}$$

where $Z_L$ is the liquid compressibility factor.

$$Z_V = \sqrt[3]{-\left(\frac{27*D - 9*B*C + 2*B^3}{54}\right) + \sqrt{R}} + \quad (V.3b)$$

$$\sqrt[3]{-\left(\frac{27*D - 9*B*C + 2*B^3}{54}\right) - \sqrt{R}} - \frac{B}{3}$$

$$Z_V = -\frac{B + Z_L}{2} \quad (V.4)$$

$$Z_V = Z_L \quad (V.5)$$

$$Z_V = \frac{-(B + Z_L) + \sqrt{(B + Z_L)^2 - 4*(C + Z_L*(B + Z_L))}}{2} \quad (V.6)$$

where in equation (V. 6), $Z_L$ is the pure liquid compressibility factor for the vapor-liquid equilibrium region determined by equation (V2.b).

Mathematics, see for example Editors: Perry R. H., Green D. W., Maloney J. O., Perry's Chemical Engineers' Handbook, 7$^{th}$ edition, McGraw-Hill, July 1999, has established that when R≧0, equation (E.1) has three roots $$Z = P + Q \quad (E.2)$$

$$Z = -\frac{P+Q}{2} + \frac{i\sqrt{3}}{2}(P-Q) \quad (E.3)$$

$$Z = -\frac{P+Q}{2} - \frac{i\sqrt{3}}{2}(P-Q) \quad (E.4)$$

Where $$P = \sqrt[3]{\frac{-1}{2}\{27*D - 9*B*C + 2*B^3\} + \sqrt{R}} \quad (E.5)$$

$$Q = \sqrt[3]{\frac{-1}{2}\{27*D - 9*B*C + 2*B^3\} - \sqrt{R}} \quad (E.6)$$

As is shown in FIG. 2, the method of the present invention starts with the calculation of R using equation (V.1). If R>0, there is, as is shown in equations E.2 to E.4, only one real root and two complex conjugate roots. The one real root represents a solution either in the pure vapor region or in the pure liquid region.

The method proceeds to equation (V.2a) where it determines if the square root of R is greater than a certain mathematical value. If this is false then the compressibility factor is in a vapor region. The vapor compressibility factor value is accepted as the pure vapor compressibility factor determined from equation (V.3b).

If the evaluation of equation (V.2a) determines that the square root of R is greater than a certain value then the compressibility factor is in a liquid region. The method proceeds first to equation (V.3a) to obtain the pure liquid compressibility factor. It then applies correction as in equation (V.4) to obtain the vapor compressibility factor and finally it accepts the higher of the two values, V.3a or V.4, as actual vapor compressibility factor as in equation (V.5).

If R=0 then all three roots of CEOS are real. Out of these three roots, at least two are equal. This condition is however lumped with the condition R<0 to avoid discontinuities.

When R<0, then all three roots given by equations (E.2), (E.3), and (E.4) are real and unequal. This represents a vapor-liquid equilibrium region. But the roots given by equations (E.2), (E.3), and (E.4) are unrealistic. Instead, the roots given by equation (V.2b) are mathematically accepted. Corresponding liquid and vapor compressibility factors are evaluated by equations (V.2b) and (V.6) respectively. The greater of these two values, V.2 or V.6, is accepted as a true vapor compressibility factor for the vapor-liquid equilibrium region.

Calculations for $Z_L$, Liquid Compressibility Factor

The algorithm follows the CEOS solution in the liquid region. It uses vapor compressibility as the extension of liquid compressibility in the vapor region. Equation V.2b is used to smooth out the $Z_L$ calculations during the transition from vapor to vapor-liquid to liquid region. Again the logic behind this framework of equations, the flowchart for which is shown in FIG. 3, is same as that discussed for vapor compressibility factor calculations.

$$\frac{dZ_L}{dT} = -\frac{\left[Z_L^2 \frac{dB}{dT} + Z_L \frac{dC}{dT} + \frac{dD}{dT}\right]}{3*Z_L^2 + 2*B*Z_L + C} \quad (L.1)$$

$$Z_L = \left(0.25 + \left(\frac{27*D - 9*B*C + 2*B^3}{54}\right) + \sqrt{R}\right) * \frac{Z_V}{0.25} + \left(\frac{27*D - 9*B*C + 2*B^3}{54} - \sqrt{R}\right) * \left(\frac{B + Z_V}{2*0.25}\right) \quad (L.2)$$

$$Z_L = -\frac{\frac{dD}{dT}}{\frac{dC}{dT}} \quad (L.3)$$

When $R \leq 0$ in the vapor-liquid equilibrium region, the compressibility factor given by equation (V.2b) is used.

When R>0 the solution lies either in the pure liquid region or the pure vapor region. Equation V.2a is determined and if it is true then the pure liquid phase is assumed. Otherwise if equation V.2b is false then the pure vapor phase is assumed.

In the pure liquid phase, first the liquid compressibility factor is determined using equation (V.3a). Then the local analytical derivative of liquid compressibility factor is determined using equation (L.1). If the derivative is $\geq 0$ then the pure liquid compressibility factor is accepted as it is. If the derivative is less than zero then a modified liquid compressibility factor given by simplified equation (L.3) is used to avoid the unrealistic solution region.

In the pure vapor phase, first the vapor compressibility factor given by equation (V.3b) is determined. Equation (L.2) then uses this vapor compressibility factor to evaluate a pseudo liquid compressibility factor as an extension of the vapor compressibility factor.

The Soave-Redlich-Kwong, Peng-Robinson, Redlich-Kwang, and Ideal forms of the CEOS have all been used to validate the method of the present invention for solving the CEOS for the compressibility factor.

It should be appreciated that the method of the present invention can accelerate the calculations of physical property by using ideal property values as initial guesses for iterative calculations, reusing earlier calculation results, either intermediate or final, after they have been generated. Further two types of caches to hold previous calculation results, namely, the intermediate results cache and the final results cache can be designed. With the intermediate results cache, once a quantity such as a compressibility factor has been generated to calculate a certain physical property, it can be reused for evaluating other properties for the same inputs. With the final results cache, a property has been calculated through linear extrapolation using the value of the property and its derivatives that have been obtained before for delta change in conditions.

Appropriate scaling factors are incorporated to account for different variations in mathematically related values. For example, the exponential relationship between vapor pressure and temperature is accounted for, by using natural log of vapor pressure while linearly changing temperature during iterative procedures.

Figure 4:
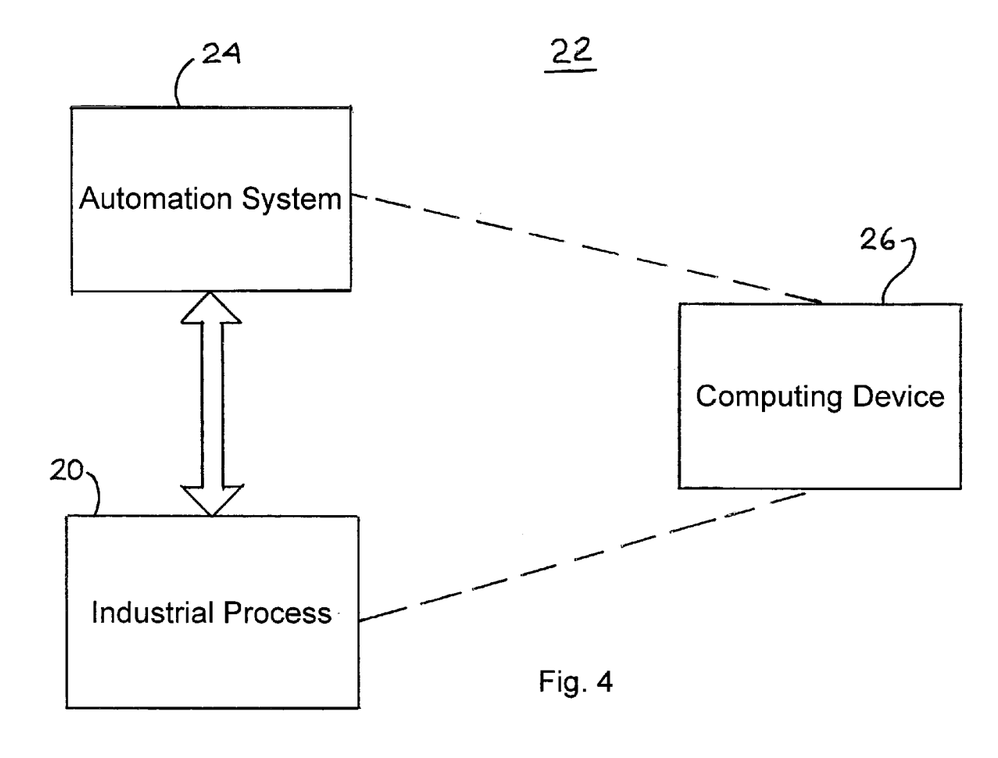
FIG. 4 shows in block diagram form a process plant in which the method of the present invention can be used.

As can be appreciated by those of ordinary skill in the art, the present invention may be used in connection with any industrial process that uses gases, liquids and their mixtures. Examples of such processes include, without limitation, those related to oil & gas, chemical, petroleum and pulp & paper. As is shown in FIG. 4, the industrial process 20 usually resides in a plant 22 which also has an automation system 24 for measurement and control of the process 20 in a manner well known to those in the art. The method of the present invention may reside on a computer readable medium and thus can be loaded into a computing device 26 such as a personal computer. The computing device 26 may, as is shown by the dotted lines, be associated with the industrial process 20 if only measurements are desired or a part of or associated with the automation system 24 if both measurement and control is desired or associated with both process 20 and system 24.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A method for calculating the compressibility factors of a mixture using the cubic equation of state (CEOS), said mixture having a liquid region, said method comprising:
   a) calculating a pure liquid compressibility factor when said compressibility factor is in said liquid region;
   b) using the second virial coefficient of said CEOS to determine from said pure liquid compressibility factor a vapor compressibility factor extensible in said liquid region; and
   c) accepting the higher of said pure liquid compressibility factor or said vapor compressibility factor extensible in said liquid region.

2. The method of claim 1 further comprising determining that said compressibility factor is in said liquid region.

3. The method of claim 1 wherein said mixture has a vapor region and said method further comprises determining that said compressibility factor is in said vapor region and accepting a pure vapor compressibility factor when said compressibility factor is in said vapor region.

4. A method for calculating the compressibility factors of a mixture using the cubic equation of state (CEOS), said mixture having a vapor-liquid equilibrium region, said method comprising:
   a) determining that said compressibility factor is in said vapor-liquid equilibrium region;
   b) calculating when said compressibility factor is in said vapor-liquid equilibrium region a pure liquid compressibility factor;
   c) using the virial coefficients of said CEOS and said pure liquid compressibility factor calculated when said compressibility factor is in said vapor-liquid equilibrium region to determine a vapor compressibility factor in said vapor-liquid equilibrium region; and
   d) accepting the higher of said pure liquid compressibility factor calculated when said compressibility factor is in said vapor-liquid equilibrium region or said vapor compressibility factor calculated in said vapor-liquid equilibrium region.

5. A method for calculating the compressibility factors of a mixture using the cubic equation of state (CEOS), said mixture having a vapor-liquid equilibrium region, said method comprising:
   a) calculating a pure liquid compressibility factor for said vapor-liquid equilibrium region;
   b) using the virial coefficients of said CEOS and said pure liquid compressibility factor calculated for said vapor-liquid equilibrium region to determine a vapor compressibility factor in said vapor-liquid equilibrium region; and
   c) accepting the higher of said pure liquid compressibility factor calculated for said vapor-liquid equilibrium region or said vapor compressibility factor calculated in said vapor-liquid equilibrium region.

6. A method for calculating the compressibility factors of a mixture using the cubic equation of state (CEOS), said mixture having a liquid region and a vapor-liquid equilibrium region, said method comprising:
   determining that said compressibility factor is either in said liquid region or in said vapor-liquid equilibrium region;
   said method when said compressibility factor is in said liquid region comprising:
   calculating a pure liquid compressibility factor;
   using the second virial coefficient of said CEOS to determine from said pure liquid compressibility factor a vapor compressibility factor extensible in said liquid region; and
   accepting the higher of said pure liquid compressibility factor or said vapor compressibility factor extensible in said liquid region;
   said method when said compressibility factor is in said liquid region comprising:
   calculating a pure liquid compressibility factor;
   using the virial coefficients of said CEOS and said pure liquid compressibility factor to determine a vapor compressibility factor in said vapor-liquid equilibrium region; and
   accepting the higher of said pure liquid compressibility factor or said vapor compressibility factor calculated in said vapor-liquid equilibrium region.

7. A method for calculating the compressibility factors of a mixture using the cubic equation of state (CEOS), said mixture having a liquid region and a vapor-liquid equilibrium region, said method comprising:
   a) calculating a pure liquid compressibility factor when said compressibility factor is in said liquid region;
   b) using the second virial coefficient of said CEOS to determine from said pure liquid compressibility factor a vapor compressibility factor extensible in said liquid region; and
   c) accepting the higher of said pure liquid compressibility factor or said vapor compressibility factor extensible in said liquid region;
   d) calculating a pure liquid compressibility factor for said vapor-liquid equilibrium region;
   e) using the virial coefficients of said CEOS and said pure liquid compressibility factor calculated for said vapor-liquid equilibrium region to determine a vapor compressibility factor in said vapor-liquid equilibrium region; and
   f) accepting the higher of said pure liquid compressibility factor calculated for said vapor-liquid equilibrium region or said vapor compressibility factor calculated in said vapor-liquid equilibrium region.

8. A method for calculating the liquid compressibility factor of a mixture using the cubic equation of state (CEOS), said mixture having a liquid region, said method comprising:
   a) calculating a pure liquid compressibility factor when said compressibility factor is in said liquid region;
   b) determining that the rate of change of said pure liquid compressibility factor with temperature is or is not less than zero; and c) accepting said pure liquid compressibility as said liquid compressibility factor when said pure liquid compressibility factor rate of change is not less than zero.

9. The method of claim 8 further comprising:
calculating said liquid compressibility factor as the ratio of the change with temperature of two of the virial coefficients of said CEOS when said pure liquid compressibility factor rate of change is less than zero.

10. The method of claim 8 further comprising:
determining that said compressibility factor is in said liquid region.

11. The method of claim 1 wherein said method is executed in a computing device in an industrial plant, said industrial plant comprising an industrial process, an automation system connected to said process, said computing device associated either with said process or said automation system.

12. The method of claim 5 wherein said method is executed in a computing device in an industrial plant, said industrial plant comprising an industrial process, an automation system connected to said process, said computing device associated either with said process or said automation system.

13. The method of claim 8 wherein said method is executed in a computing device in an industrial plant, said industrial plant comprising an industrial process, an automation system connected to said process, said computing device associated either with said process or said automation system.

14. A computer readable medium having instructions for causing a computer to execute a method for calculating the compressibility factors of a mixture using the cubic equation of state (CEOS), said mixture having a liquid region, said instructions comprising:
a) calculating a pure liquid compressibility factor when said compressibility factor is in said liquid region;
b) using the second virial coefficient of said CEOS to determine from said pure liquid compressibility factor a vapor compressibility factor extensible in said liquid region; and
c) accepting the higher of said pure liquid compressibility factor or said vapor compressibility factor extensible in said liquid region.

15. A computer readable medium having instructions for causing a computer to execute a method for calculating the compressibility factors of a mixture using the cubic equation of state (CEOS), said mixture having a vapor-liquid equilibrium region, said instructions comprising:
a) calculating a pure liquid compressibility factor for said vapor-liquid equilibrium region;
b) using the virial coefficients of said CEOS and said pure liquid compressibility factor calculated for said vapor-liquid equilibrium region to determine a vapor compressibility factor in said vapor-liquid equilibrium region; and
c) accepting the higher of said pure liquid compressibility factor calculated for said vapor-liquid equilibrium region or said vapor compressibility factor calculated in said vapor-liquid equilibrium region.

16. A computer readable medium having instructions for causing a computer to execute a method for calculating the compressibility factors of a mixture using the cubic equation of state (CEOS), said mixture having a liquid region, said instructions comprising:
a) calculating a pure liquid compressibility factor when said compressibility factor is in said liquid region;
b) determining that the rate of change of said pure liquid compressibility factor with temperature is or is not less than zero; and
c) accepting said pure liquid compressibility as said liquid compressibility factor when said pure liquid compressibility factor rate of change is not less than zero.

* * * * *